United States Patent [19]

Beck

[11] Patent Number: 4,705,073
[45] Date of Patent: Nov. 10, 1987

[54] MOLDED PLASTIC GATE VALVE AND SEALING MEANS THEREFOR

[75] Inventor: Blaine E. Beck, Peachtree City, Ga.

[73] Assignee: Advanced Medical Devices, Inc., Dover, Del.

[21] Appl. No.: 854,829

[22] Filed: Apr. 23, 1986

[51] Int. Cl.⁴ .............................................. F16K 11/06
[52] U.S. Cl. ........................... 137/625.25; 128/205.19;
128/205.24; 137/625.45; 137/625.48; 604/26;
604/31; 604/33
[58] Field of Search ...................... 128/205.19, 205.24;
137/596.12, 625.25, 625.45, 625.48, 872, 875;
251/193, 284, 326, 327; 604/26, 31, 33, 45, 119,
129, 249

[56] References Cited

U.S. PATENT DOCUMENTS

| | | | |
|---|---|---|---|
| 3,035,809 | 5/1962 | Dickinson | 251/193 |
| 3,113,757 | 12/1963 | Nixon | 251/327 X |
| 3,457,950 | 7/1969 | Over | 251/327 X |
| 3,570,540 | 3/1971 | McInnes et al. | 137/625.48 |
| 3,784,158 | 1/1974 | Cave | 251/327 |
| 3,936,031 | 2/1976 | Berman et al. | 251/284 |
| 4,019,535 | 4/1977 | Buckethal | 251/193 X |
| 4,193,406 | 3/1980 | Jinotti | 128/205.19 X |
| 4,221,307 | 9/1980 | Peterson | 251/327 X |
| 4,595,005 | 6/1986 | Jinotti | 128/205.24 |

FOREIGN PATENT DOCUMENTS 946258  7/1956  Fed. Rep. of Germany ............ 128/205.19

Primary Examiner—Gerald A. Michalsky
Attorney, Agent, or Firm—Schweitzer & Cornman

[57] ABSTRACT

A gate or slide valve of molded plastic construction having a flat gate or slide member reciprocable or rotatable in a slot whose widths may vary due to the limitations of the molding process in combination with a flat low-friction laminated seal which is resiliently adjustable to accommodate the aforesaid widthwise variations.

7 Claims, 9 Drawing Figures

MOLDED PLASTIC GATE VALVE AND SEALING MEANS THEREFOR

BACKGROUND OF INVENTION

This invention concerns a valve of all-molded plastic construction and improvements in the design of one or more sealing means which are incorporated therein to render sealing more efficient while greatly reducing cost. Such valves may have particular application in systems for suctioning fluids from the lungs and alternatively, for oxygenating the lungs of patients requiring such treatment and as such may be made sufficiently inexpensively to be disposable.

Gate valves (often called slide valves) operate on the same basic principle. The housing or body of the valve contains one or more inlets and connected thereto, passages through the housing which conduct fluids to one or more outlets. The housing includes a recess or slot which receives the slide member or gate, often a flat rectangular or semi-circular member. The slide member contains one or more fluid passages or apertures which can be selectively aligned by reciprocation or rotation of the slide member with one or more through passages in the housing or valve body, thus controlling or limiting flow through the valve.

Attempts have been made to produce valves of this type by molding the housing and slide member of plastic, for example by injection molding. This type of manufacture obviously can produce a valve less expensively than for example, where the parts are of metal and particularly where machining and precision fitting of parts is required. However, it is difficult, if not impossible to maintain close tolerances, using present injection molding techniques, between the dimensions of the slide member and the recess in the valve housing which receives the slide member. In order to produce an efficient valve, where sealing is effected directly (without the interposition of specific sealing means) between slide member and valve housing, the difference in width between the slide member and its recess would have to be held to say, one-half thousandths of an inch (0.0005"). It is not unusual when molding valves of this type however to be unable to hold tolerances of less than plus or minus five thousandths. The use of conventional seals in such circumstances will not satisfactorily solve these wide dimensional differences, and it has been found that to attempt efficient sealing would be to introduce large frictional forces which inhibit movements of the slide member. It is one of the important aspects of the present invention to solve these inherent problems in the manufacture of molded plastic valves of this type.

In the environment in which the present invention is depicted herein, one side of the valve is connected to a source of suction and to an oxygen source, the outlet of the valve being connected to a catheter which passes into the lungs of a patient to be treated. The valve body has fluid passages therethrough which extend from the inlet openings to a single outlet, the valve body further defining a recess perpendicular thereto which receives a slide member or gate. The latter is reciprocable or rotatable and defines at least one opening which can be selectively aligned with the aforesaid fluid passages to prevent or interrupt flow to the outlet. Within the oxygenation/suctioning environment, illustrations of systems and valves of this type, may be found in U.S. Pat. Nos. 4,193,406 and 4,300,550.

A serious problem shared by these prior valve constructions is their lack of adequate sealing between slide member and fluid passage orifices which greatly impairs the efficiency of the systems incorporating them. Where, for example, fluid is suctioned from, and oxygen is alternatively provided to the lungs, it is imperative and apparent that each operation be performed as expeditiously as possible to minimize potential harm to the patient and leakage of oxygen or bacterially contaminated air to the surrounding environment. Therefore, generally speaking, one of the important aspects of the present invention is to provide improved sealing means which obviates the above difficulties and which is expected to have use in many other applications other than the disclosed oxygenation/suctioning system. The sealing construction disclosed herein (which is a laminated seal) has been used heretofore as a gasket (engines) and as a seal around aircraft canopies and exit doors and has been used to seal medicinal ampules or vials; as used herein it is a significant improvement over the foregoing applications and valve and other sealing configurations found for example in U.S. Pat. Nos. 4,089,506; 3,907,310; 4,111,440; 4,019,535; 4,465,062; 4,538,607.

As will be described, the gate valve sealing means of the invention particularly finds application in inexpensive molded plastic valves which may have to be disposable for hygienic reasons; i.e. in hospital environments. The improved seal construction significantly reduces the cost of molding the body of the valve; maintaining close tolerances to achieve effective sealing; and the cost of the plastic materials chosen for particular valve construction, while simultaneously providing greatly increased sealing efficiency.

Other improved features of the new valve construction include an improved non-contaminating valve venting system will become apparent upon examination of the detailed description and drawing.

SUMMARY OF INVENTION

In accordance with the present invention, there is disclosed a valve having a housing of molded plastic material, the housing having a recess to receive an elongated, flat-sided member for slidable movement therein with respect to said housing, the housing having fluid passage means therethrough, the fluid passage means defining aligned, facing orifices in the recess, the slidable member also defining fluid passage means adapted to be brought into and out of alignment with the fluid passage means in the housing, the slidable member including sealing means comprising a laminated member defining fluid passage means generally congruent with the fluid passage means in said member. The laminated member has an outer layer of low friction plastic material (for example polytetrafluorethylene or Teflon) and bonded thereto, an inner layer of resilient material (for example silicone rubber) the layer of resilient material normally being maintained in compression when said slidable member is in the recess in the housing, the outer low friction plastic layer being thereby thrust into sealing contact with the facing portions of the housing.

The invention further includes venting means which is located in the housing on the side thereof closest to the inlet connections for the housing so that contamination from the area in which the slide member is located is substantially obviated. The housing includes a special lavage port to permit the introduction of a sterile saline solution as an adjunct to the oxygenation/suctioning procedure. Another aspect of the invention is the manner in which the rotary or reciprocable slide member is held in its recess in the valve housing by resilient tab means which acts as a stop to limit movement of the slide member and which secures the slide member in its recess.

DESCRIPTION OF PREFERRED EMBODIMENTS

Figure 1:
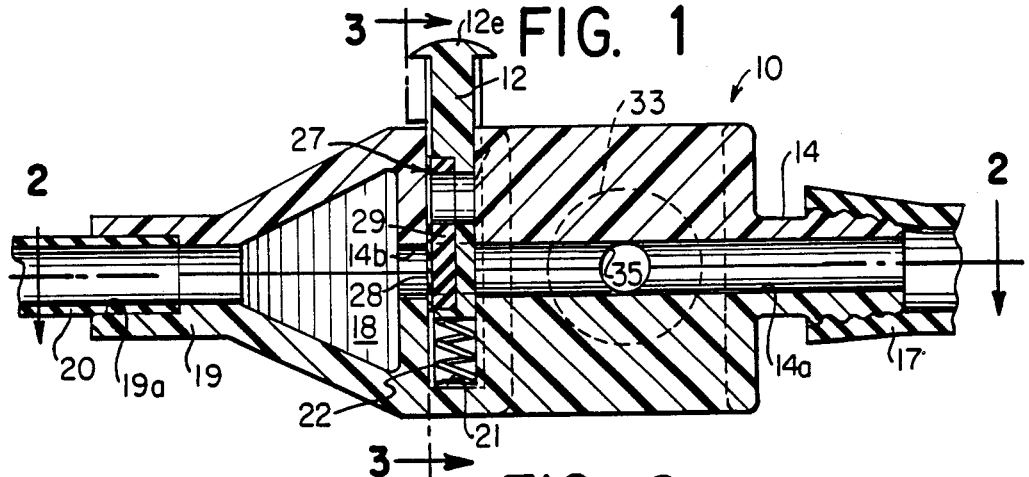
FIG. 1 is a side, cross-sectional view of a molded plastic valve embodying the principles of the invention.
Figure 2:
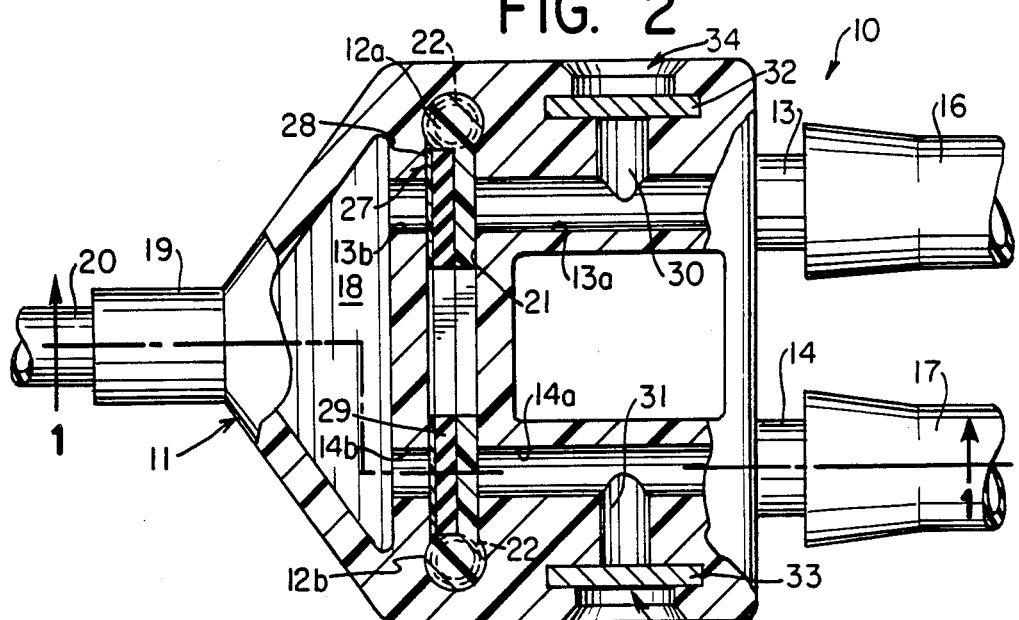
FIG. 2 is a plan view partially broken-away and partially in cross-section of the valve of FIG. 1.
Figure 3:
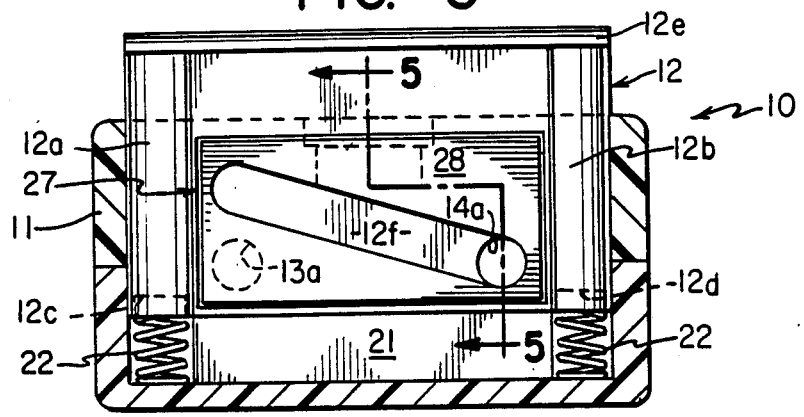
FIG. 3 is a view taken in the direction of Arrows 3—3 of FIG. 1.

Referring now to the drawing and initially to FIGS. 1-3 thereof a valve 10 embodying the principles of the invention has been illustrated. The valve 10 includes a one-piece housing 11 and a moveable slide member 12 which are each molded of a suitable plastic material, by the use of injection molding techniques. Housing 11 has tubular inlet connections 13 and 14 which are threaded to plastic tubing 16 and 17. One of the uses of the valve 10 is in conjunction with oxygenation/suctioning systems which permit the alternate oxygenating of the lungs of a patient and the removal of fluid therefrom by suction. Accordingly and for illustrative purposes, tubular member 16 may be for example connected to a source of suction and member 17 connected to a source of oxygen.

The housing 11 includes passages 13a and 14a respectively which are in alignment with passages 13b, 14b. The latter are connected with a chamber 18 which is connected to a single cylindrical outlet 19. Outlet 19 is internally recessed at 19a to receive the end of catheter 20 whose distal end (not shown) may be inserted into the lungs of a patient for oxygenation/suctioning treatment.

Between the inner ends of passages 13a, 14a, and 13b, 14b housing 11 defines a generally rectangular slot or recess 21 which receives the slide member 12 for reciprocal movement therein. The lateral ends of slide member 12 have been formed as cylindrical guide sections or posts 12a and 12b which are received within mating cylindrical end sections 21a, 21b of housing recess 21. The inner ends of post sections 12a and 12b define two laterally spaced recesses 12c and 12d which receive coiled compression springs 22, the opposite ends of these springs resting upon the bottom surface 21c of recess 21. Slide member 12 can be depressed by the therapist or doctor administering the oxygenation/suctioning treatment by pressing down with thumb or forefinger against the upper curved flange 12e of the slide member, the inner portion of which serves to limit inward movement of the slide member into recess 21. When such pressure is released, springs 22 will return the slide member 12 to the position shown in the figures (which in the illustrated embodiment is the oxygenation position) when downward pressure has been released from the flange 12e of the slide member. Slide member 12 defines a generally elliptical aperture 12f which in the full outer position shown in FIGS. 1 and 3 becomes aligned with the tube 17 connected to the oxygen source, while as best seen in FIG. 3 when slide member 12 is depressed within recessed 21, the elliptical aperture 12b is out of alignment with passageway 14a (oxygen) and is brought into alignment with passageway 13a (suction).

Figure 5:
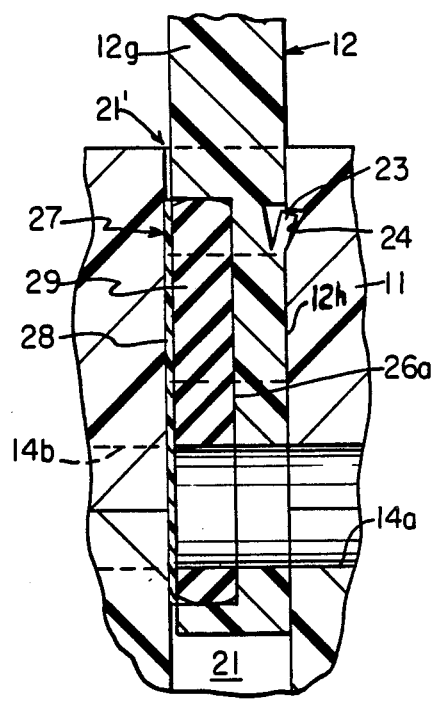
FIGS. 5 and 6 are enlarged cross-sectional views of the reciprocable slide member and laminated seal of the invention which illustrate the ability of the seal to compensate for differences in the width of the slide recess.
Figure 6:
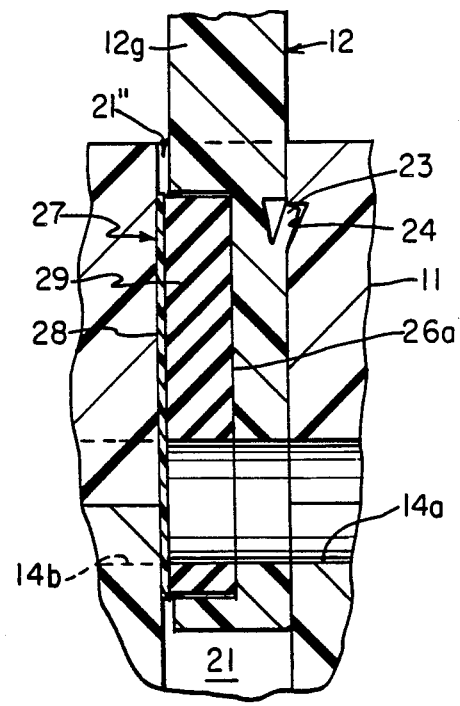

Referring now to FIGS. 5 and 6, it will be seen that slide member 12 has been formed to have an integral leaf spring tab 23 which normally and resiliently projects from a lateral surface of the slide member. Housing 11 has been formed with a corresponding recess 24 which receives tab 23 when the slide member 12 has been inserted into housing recess 21 for a distance sufficient to permit tab 23 to spring outwardly and into recess 24. When this has occurred, tab 23 acts as a stop adapted to bear against the upper edge of recess 24 to prevent movement of slide member 12 outwardly of the recess beyond the position shown in FIGS. 5 and 6. It will be understood that when the slide member 12 is further depressed into the recess and into its alternate suction position, tab 23 will be urged out of engagement with recess 24 and will return into such engagement to limit outward movement of slide member 12 when the parts have re-assumed the position of FIGS. 5 and 6.

In accordance with a critical aspect of the present invention, it will be seen that one side of slide member 12 defines a generally rectangular recess 26 and that within such recess a laminated sealing member 27 is mounted and affixed by using, for example, a suitable adhesive. Seal 27 consists of two layers, adhesively bonded together, the outermost layer 28 facing passages 13b and 14b comprising a layer of low friction plastic material such as Teflon (polytetrafluorethylene) while the inner layer 29 within recess 26 is resilient and may, for example, be of silicone rubber. The laminated seal 27 extends peripherally around elliptical aperture 12f in slide member 12. It will be seen and understood (See FIG. 5) that surface 12g of slide member 12 and surface 26a (within recess 26) are planar and parallel and that laminated seal 27, including low friction sheet 28 is planar as well and parallel to these surfaces of slide member 12. In fact the outer surface of sheet 28 facing the orifice ends of passages 13b and 14b may be perceived as a projection of the surface 12g of slide member 12, but resiliently and movably backed up by layer 29.

The unique qualities of laminated seal 27 to effect sealing of the elliptical passage 12d in the slide member 12 with respect to passages 13b and 14b (and also with respect to passages 13a and 14a) may be seen in FIGS. 5 and 6. Note the differences in dimension between the relatively narrow gap 21' shown in FIG. 5 and the relatively wider gap 21" shown in FIG. 6 which occurs between the surface 12g of the slide member and the opposing or facing surface 11a of the housing. These differences in width may in an actual molded valve configuration represent five thousands (0.005) of an inch, a fairly typical working tolerance for injection molded plastic valves of this type. Thus the relatively smaller gap 21' (FIG. 5) causes the resilient layer 29 of seal 27 to be more greatly compressed than in the configuration of FIG. 6. However since resilient layer 29 is constantly in compression, in both configurations it operates to force the low friction sheet 28 facing passages 13b and 14b into sealing engagement with the orifice ends of passages 13b and 14b. Conversely, the resilient thrust of layer 29 also acts to force surface 12h facing passages 13a and 14a into sealing engagement with the orifice ends of these passages, thereby effecting a complete seal between both sides of the slide member and the passages in the adjacent housing.

In accordance with another aspect of the present invention, the valve 10 incorporates a venting system which is best seen in connection with FIG. 2. Each of passages 13a (suction) and 14a (oxygen) includes respectively vent passages 30, 31 which further include check valves 32, 33 to control venting of passages 13a, 14a through vent orifices 34, 35. Check valves 32 and 33 may for example be of a slitted diaphram type and will each be set to open whenever a preselected pressure differential exists with respect to opposite sides of the diaphram. Accordingly, should a blockage occur in a catheter during the suctioning mode, air would be admitted through check valve 32 into passage 13a as soon as a requisite pressure differential exists between the reduced pressure in passage 13a and atmospheric pressure. Likewise should an oxygen pressure surge (which could be very harmful to a patient, particularly an infant, whose lungs are being oxygenated) occur in line 14a, oxygen would be vented through valve 33 to the atmosphere to relieve the pressure surge.

The valve 33 has one other useful function. The slitted diaphram construction will permit the introduction therethrough of needle and accompanying sterile saline solution for lavage. The ability of the valve 10 quickly and easily to alternate between suction and oxygenation modes permits such saline solution to break up mucous or other blockages from the lungs encountered during suctioning by lavage which will be simultaneously administered with oxygen until suction flow is re-established and the lungs are completely clear.

It will be noted that passages 30, 31, and valves 32, 33 are positioned relative to slide member 12 and housing recess 24 so that any bacterial contamination from member 12 or recess 21 cannot issue from vent orifices 34 or 35 when check valves 32, 33 are open. Thus suction line 13a leading to the suction pump exhaust venting system (not shown) remains free from contamination. Similarly if oxygen is vented to atmosphere through valve 33 and vent orifice 35, the surrounding enviroment remains uncontaminated. These are very important health considerations particularly to those personnel present during administration of the oxygentation/suctioning procedure.

Figure 4:
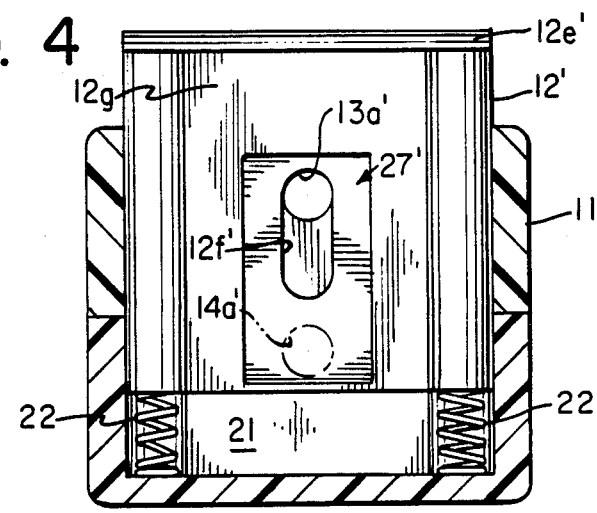
FIG. 4 is an end view, partially in cross-section of an alternate embodiment of the invention showing in particular an alternate arrangement of the passages in the valve housing and in the reciprocable slide member.

FIG. 4 illustrates a variation of the valve configuration disclosed in FIGS. 1-3. Parts which are the same have been designated by the same reference numerals. Accordingly, valve housing 11 has been formed to have slide recess 21 therein which receives slide member 12'. In the configuration of FIG. 4, it will be seen that oxygen passage 13a' is located above suction passage 14a' and not side-by-side as in the previous embodiment. Consequently, aperture 12f' in the slide member is vertically oriented, as is laminated seal 27'. Otherwise, the aperation and function of the valve configuration of FIG. 4 is the same as that described in connection with FIGS. 1-3 and FIGS. 5 and 6.

Figure 7:
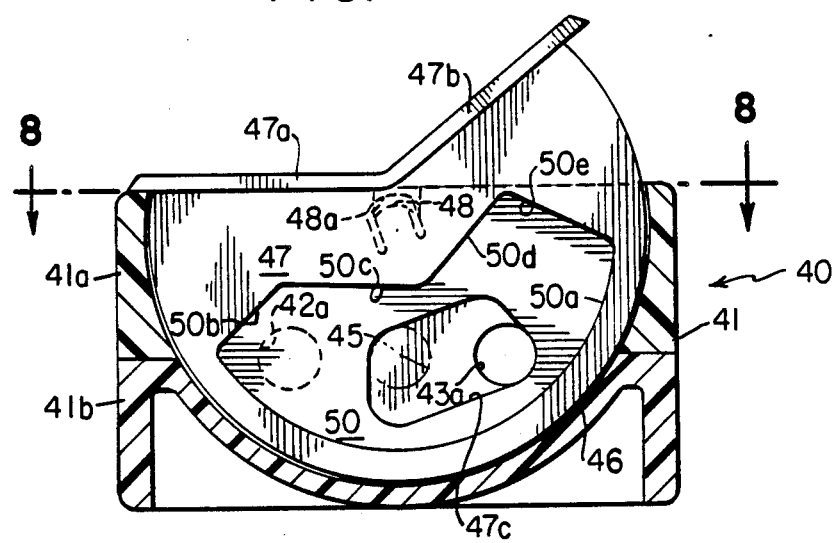
FIGS. 7 and 8 are respectively end and plan views of an alternate rotary form of valve incorporating the features of the invention.
Figure 8:
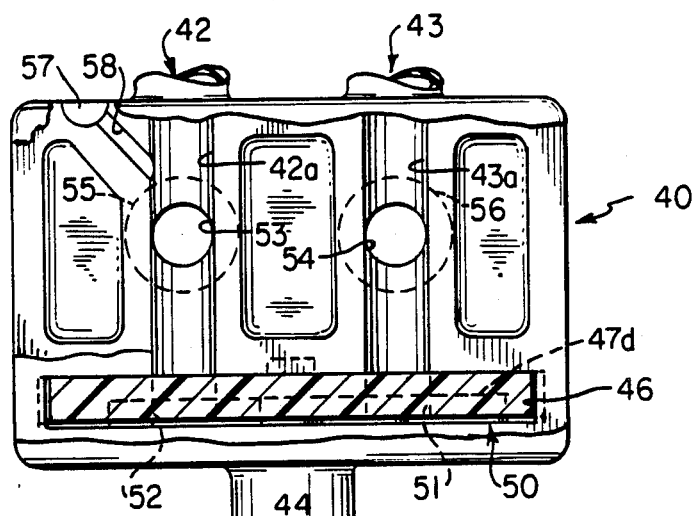
Figure 9:
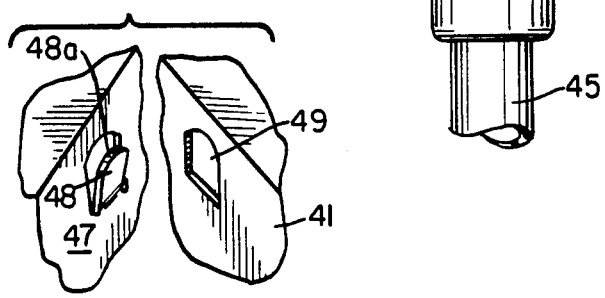
FIG. 9 is a fragmentary illustration of the rotary slide member of FIGS. 7 and 8 and the adjacent housing, juxtaposed to show the tab stop and recess means therefor of the invention.

Referring now to FIGS. 7-9 there has been shown an alternate rotary valve 40 constructed according to the principles of the present invention. Valve 40 includes plastic valve housing 41 molded in two part 41a and 41b, the housing having separate inlets 42, 43 (which may be connected to suction and oxygen respectively ) and a single outlet 44 connected to catheter 45. Passages 42a, 43a are formed within housing 41 and lead to a generally semi-circular recess 46 which receives rotary slide member 47 therein. The latter includes an integral resilient tab 48 the upper curved end 48a of which is adapted to be received and to snap into a mating recess 49 (FIG. 9) in the rotary slide member when the parts are assembled. The slide member has been formed with outer flanges 47a, 47b each of which can be alternately depressed by the therapist or doctor to rotate member 47 into the oxygenation or suctioning positions. Flanges 47a and 47b will abut the housing 41 to define these two operational positions. Rotation of slide member 47 is about the curved end portion 48a of tab 48 and correspondingly curved portion of recess 47a.

Slide member 47 defines an aperture 47c therein which will register with one or the other of passages 42a, 43a when member 47 assumes its alternate positions. Accordingly and by this means alternate fluid connection can be made of inlets 42 and 43 to outlet 44. Slide member 47 further defines a recess 47d which receives a laminated seal 50 whose periphery includes the curved section 50a and straight peripheral sides 50b-50e. Seal 50 is a bonded laminate of two layers, i.e., resilient backing layer 51 (adhesively mounted in recess 47d) and low friction sheet 52, which faces the inner orifice end of outlet 44. The operation of laminated seal 50 is the same as described in respect of the seal 27 of FIGS. 1-6. It will therefore be understood that the combination of constant resilient force applied by resilient backing 51 acting upon the low friction surface of sheet 52 produces a highly efficient sealing of both sides of slide member 47 with respect to the orifice ends of the passages through the valve 40 and that seal 50 is capable of compensating for the fairly large molding tolerances which occur between the respective widths of recess 46 and the rotary slide member 47.

Valve 40 also includes the non-contaminating vent system described in connection with the first embodiment. For this purpose, vent orifices 53, 54 and slitted diaphragm check valves 55, 56 have been illustrated in FIG. 8. Additionally, valve 40 has been provided with a lavage port 57 and passage 58 through which a needle may be inserted to inject a sterile saline solution into the oxygen passage 42a. The lavage procedure has been described in connection with the embodiment of FIGS. 1-6. It will be noted that lavage passage 58 is very narrow (sufficiently wide to admit a needle) and consequently when oxygen is flowing in passage 42a and passage 58 is not in use, ambiant air will be aspirated into this passage by the venturi effect produced by the flow of oxygen past the inner end of passage 58.

The various valve configurations disclosed herein are ideally of all molded plastic construction and lend themselves to high production and inexpensive cost. The laminated seal disclosed herein provides extremely efficient low-friction sealing and makes possible the use of these inexpensive molded plastic techniques.

It will be understood that the foregoing description has related to particular embodiments of the invention which are representative. In order to understand the scope of the invention, reference should be made to the appended claims.

I claim:

1. In an oxygenation/suctioning valve or the like of the type comprising a molded plastic valve body having oxygenation and suctioning port means at one side and catheterization port means on an opposite side thereof, a plastic valve member bi-directionally movable in said valve body between limit positions and having valve passage means therein for selectively connecting said catheterization port means to said oxygenation, in one limit position, and to said suctioning port means, in the other limit position, the improvement characterized by
    (a) said valve body being of precision molded construction and having an open valve cavity formed therein for the movable reception of said valve member,
    (b) said oxygenation and suctioning port means opening into said valve cavity at one side, and said catheterization port means opening into said valve cavity at the other side,
    (c) said valve member being of precision molded construction and having a cross sectional configuration closely conforming to that of said valve cavity while being freely bi-directionally movable therein with at least a minimum positive clearance,
    (d) said valve member having an an open recess of predetermined depth, less than the thickness of said valve member, and formed in at least one side thereof,
    (e) a resilient valve seal member received in said recess and projecting outward therefrom, and having an outer surface of low friction material,
    (f) said resilient seal member having a thickness, greater than the depth of said recess, such that, within normal precision molding tolerance limits of said valve cavity and said valve member, said seal member will be held under at least some compression within said recess,
    (g) said valve member and seal member having passage means therein, within the area of said recess, for alternatively connecting said oxygenation or suctioning port means with said catheterization port means, and
    (h) said valve member and said valve body having cooperating limit stop means for limiting the bi-directional movements of the valve member and defining said limit positions,
    (i) said seal-receiving and said seal extending over an area of said valve member such that at least a portion of said seal is positioned opposite said oxygenation and suctioning port means in either limit position of said valve member.

2. An oxygenation/suctioning valve or the like according to claim 1, further characterized by
    (a) said valve membering being of generally flat, rectangular cross sectional configuration having parallel principal opposite side faces,
    (b) said recess being formed in one side face of said valve member,
    (c) said resilient member, when under compression, serving to press the opposite side face of said valve member into sealing relation with the adjacent wall of said cavity.

3. An oxygenation/suctioning valve or the like according to claim 2, further characterized by
    (a) the depth of said recess and the thickness of said resilient seal member being substantial in relation to the amount of said positive clearance, whereby an effective seal is formed, without inhibiting free sliding movement of said valve member, over the normal tolerance range of clearances experienced in normal precision molding procedures.

4. An oxygenation/suctioning valve or the like according to claim 1, further characterized by
    (a) said cavity being of closed end configuration, opening from said body valve body at one side,
    (b) a said valve member being received in said cavity and having at least a portion thereof projecting out of the open end of said cavity and providing a manually engageable element,
    (c) one of said valve body or valve member having an integral, deflectable tab projecting toward the other,
    (d) the said other of said members being formed with a recess for receiving said deflectable tab and being operative therewith to limit movement of said valve member in a direction out of said cavity.

5. In an oxygenation/suctioning valve or the like of the type comprising a molded plastic valve body having oxygenation and suctioning port means at one side and catheterization port means on an opposite side thereof, a plastic valve member bi-directionally movable in said valve body between limit positions and having valve passage means therein for selectively connecting said catheterization port means to said oxygenation, in one limit position, and to said suctioning port means, in the other limit position, the improvement characterized by
    (a) said valve body and valve member being of precision molded construction, to tolerances of approximately plus or minus 0.005 inch,
    (b) said valve member being of a relatively thin, flat cross sectional configuration,
    (c) said valve body having a valve receiving cavity therein of relatively thin, flat cross sectional configuration adapted for the reception of said valve member,
    (d) said valve member and said cavity being so dimensioned that, in all instances, a positive clearance will exist between the valve member and the walls of said cavity,
    (e) valve port means in said valve body and communicating with said cavity in opposite walls thereof,
    (f) said valve member having valve passage means operable upon predetermined positioning of said valve member to connect certain of said valve port means and to block certain other port means,
    (g) said valve member, in the region of said valve passage means, having a recess of substantially greater depth than the thickness of said positive clearance,
    (h) a resilient seal member received in said recess and having a thickness at least slightly greater than the combined thickness of said positive clearance and the depth of said recess, whereby said seal member is maintained under at least a slight compression,
    (i) said seal member comprising a composite material formed principally of resilient material and having an outer surface of low friction material,
    (j) said seal member forming a seal with one wall of said cavity and urging the opposite side of said valve member toward the opposite wall of said cavity.

6. An oxygenation/suctioning valve or the like according to claim 5, further characterized by
   (a) spring means urging said valve member in one direction to one limit position, and
   (b) said valve member being manually displaceable in the opposite direction a second limit position.

7. An oxygenation/suctioning valve or the like according to claim 5, further characterized by
   (a) said valve member having an integral deflectable tab,
   (b) said valve body being formed with a recess in one wall of said cavity engageable with said tab to retain said valve member in said recess.

* * * * *